United States Patent [19]

Howes et al.

[11] 4,036,814
[45] July 19, 1977

[54] LIGHTLY CROSS-LINKED HYDROGEL FORMED FROM N-VINYL LACTAM AND HYDROPHOBIC ACRYLIC ESTER COMONOMER

[75] Inventors: John Gordon Bernard Howes, Hertford Heath; Nicholas Mario da Costa; Rupert Alec Selway, both of Harlow; William Duncan Potter, Puckeridge, all of England

[73] Assignee: Warner-Lambert Company, Morris Plains, N.J.

[21] Appl. No.: 590,037

[22] Filed: June 25, 1975

[30] Foreign Application Priority Data

July 4, 1974 United Kingdom ............... 29757/74
Apr. 28, 1975 United Kingdom ............... 17586/75

[51] Int. Cl.² .......................................... C08F 26/08
[52] U.S. Cl. ..................... 260/47 UA; 260/63 UY; 526/264; 526/265
[58] Field of Search .......... 260/47 UA, 80.3 N, 80.72, 260/63 UY, 86.1 R; 526/264, 265

[56] References Cited

U.S. PATENT DOCUMENTS

| | | | |
|---|---|---|---|
| 3,454,446 | 7/1969 | Sakuragi et al. | 260/86.1 |
| 3,532,679 | 10/1970 | Steckler | 260/80.72 |
| 3,629,197 | 12/1971 | Stiehl | 260/80.72 |
| 3,699,089 | 10/1972 | Wichterle | 260/78.3 UA |
| 3,708,445 | 1/1973 | Junas et al. | 260/86.1 R |
| 3,787,380 | 1/1974 | Stamberger | 260/80.72 |
| 3,792,028 | 2/1974 | Seidermann | 260/80.72 |
| 3,878,175 | 4/1975 | Steckler | 260/86.1 R |

*Primary Examiner*—Joseph L. Schofer
*Assistant Examiner*—Peter F. Kulkosky
*Attorney, Agent, or Firm*—Marn & Jangarathis

[57] ABSTRACT

A copolymeric hydrogel for contact lenses with physiological saline uptake 65–85% is formed from an N-vinyl lactam e.g. N-vinyl-2-pyrrolidone and up to 15% of a hydrophobic comonomer of formula

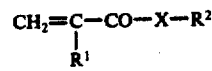

where $R^1$ is H or $C_1$–$C_4$ alkyl (preferably methyl) X is —O— or —NH— and $R^2$ is aryl, $C_1$–$C_6$ alkyl substituted by aryl or aryloxy, or $C_1$–$C_6$ alkoxy substituted by aryl or aryloxy. Preferably the aryl or aryloxy group contain one or two six-membered carbocyclic aromatic rings; they may be $C_1$–$C_4$ alkyl, $C_1$–$C_4$ alkoxy, or halogen, substituted. Crosslinking agents used preferably have their two functional groups differing in reactivity e.g. allyl, or 3-allyloxy-2-hydroxypropyl, methacrylates.

29 Claims, No Drawings

LIGHTLY CROSS-LINKED HYDROGEL FORMED FROM N-VINYL LACTAM AND HYDROPHOBIC ACRYLIC ESTER COMONOMER

This invention relates to a novel cross-linked hydrogel copolymer useful in a medical context e.g. in the manufacture of prostheses, in dialysis, or in sustained release preparations, but whose primary use is envisaged to be as a material for making contact lenses.

It is well known to make contact lenses from poly(hydroxyethylmethacrylate), otherwise known as polyHEMA. Such lenses have good strength and flexibility properties but their permeability to oxygen and their water uptake is rather low. This means that there is a danger of anoxia which can cause pain and damage to the cornea.

In other known copolymers described for instance in German OLS 2205391, lenses of higher water content are obtained with a correspondingly higher oxygen permeability. However, the strength and durability of these lenses is much diminished compared with that of polyHEMA lenses.

It has recently been proposed to make such contact lenses from copolymers of vinyl pyrrolidone (VP) and methyl methacrylate (MMA). Because there is a range of copolymers which can be made it is possible to control and improve the oxygen permeability and water uptake by selecting the requisite copolymer.

The present invention is a further development of such work which uses highly hydrophobic acrylate, alkacrylate, acrylamide and/or alkacrylamide monomers together with N-vinyl lactams to form copolymers.

In one aspect therefore the present invention consists in a lightly cross-linked hydrogel copolymeric material capable of an uptake of physiological saline of between 65% and 85% by weight based on the total weight of gel, said material being formed from (1) at least one watersoluble N-vinyl lactam and (2) as a comonomer, not more than 15 mole percent of at least one compound of formula:

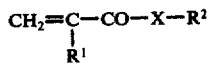

where X is —NH— or —O—; $R^1$ is hydrogen or an alkyl group of straight or branched chain containing up to 4 carbon atoms; and $R^2$ is either (a) a substituted or unsubstituted aryl group or (b) an alkyl group of straight or branched chain containing from 1 to 6 carbon atoms, substituted by at least one substituted or unsubstituted aryloxy group or (c) a hydroxyalkyl group of straight or branched chain containing from 1 to 6 carbon atoms further substituted on a carbon atom by at least one substituted or unsubstituted aryl group and/or at least one substituted or unsubstituted aryloxy group, any of the said aryloxy groups in each case not substituting the carbon atom adjacent to the —X— group.

It is preferred for the group $R^1$ to be methyl, that is to say for the compound of the formula given to be a methacrylate ester or methacrylamide.

It is preferred that the substituted alkyl group $R^2$ should contain one or (especially) two carbon atoms and that the hydroxyalkyl group should contain two carbon atoms.

The aryl or aryloxy constituent described above usually comprises one or two six-membered carbocyclic rings. It can be a mononuclear, fused binuclear or other binuclear radical.

Examples are phenyl, 2-naphthyl, (3-phenyl)phenyl, (4-phenyl) phenyl, (3-benzyl) phenyl or (4-benzyl) phenyl or the corresponding phenoxy, 2-naphthyloxy, (3-phenyl) phenoxy, (4-phenyl) phenoxy, (3-benzyl) phenoxy or (4-benzyl) phenoxy.

Optionally such aryl or aryloxy group can be substituted by one or two alkyl groups of straight or branched chain containing from one to four carbon atoms, one or two alkoxy groups of straight or branched chain containing from one to four carbon atoms, or one or two halogens. A preferred halogen is chlorine, but possibly bromine can be utilised as a substituent.

The preferred N-vinyl-lactams include N-vinyl-2-pyrrolidone, N-vinyl-2-piperidone, and N-vinyl-ε-caprolactam. The compound N-vinyl-2-pyrrolidone, hereinafter referred to as VP, is preferable.

While the Applicants do not intend to be limited by any hypothesis to the mode of action of this invention, it seems possible that the hydrophobic constituents link together to form a hydrophobic matrix within a hydrophilic matrix. Thus, if the amount of hydrophobic constituent is increased over 15 mole % the water content will be decreased and the product will be unduly stiff and show creep.

The cross-linked materials described above are formed by the addition to the monomers of a di-functional compound. The concentration of this di-functional compound or cross-linking agent is chosen according to the required degree of cross-linking. Consequently, it is determined not only by the amount of the monomers but also by their type and ability to form the cross-linked polymer. The less effective cross-linking agents have to be applied in a higher concentration that the more effective ones, and while in general up to 5% w/w of the cross-linking agent is possible it is preferred to use the more effective cross-linking agents whereby only up to 2% is preferable. Possible cross-linking agents are for instance, N,N methylenebisacrylamide, N,N-methylenebismethacrylamide, ethylene glycol dimethacrylate or polyethylene glycol dimethacrylates of general formula:

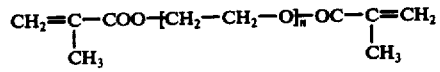

(where n is 1 to 4 and may or may not be an integer i.e. the latter when a mixture of species is present).

However, a particularly valuable form of cross-linking agent is a cross-linking agent where the two functional groups differ in reactivity, usually by virtue of their point of attachment to the remainder of the molecule. Particular examples of these are monoesters of acrylic or methacrylic acid with unsaturated aliphatic radical, e.g. allyl methacrylate or 3-allyloxy-2-hydroxy propyl methacrylate.

It is generally also envisaged to use as crosslinking agents compounds of formula:

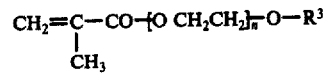

where $R^3$ is allyl or vinyl and n is 0 to 4 (preferably an integer e.g. 3, indicating that a pure species is present) or of formula:

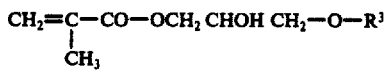

While this invention is predominantly concerned with copolymers containing two constituents, it is within the ambit of the invention to include further proportions of other copolymerizable monomers in order to modify further the properties of the eventual hydrogel.

More specifically there are also envisaged, according to the present invention terpolymers (or higher order copolymers) containing two or more hydrophobic monomers and one hydrophilic monomer, e.g. a phenethyl methacrylate/2-naphthyl methacrylate/VP terpolymer.

While moreover this invention is primarily concerned with bulk polymerisation, involving crosslinking, with mechanical shaping of the desired cross-linked copolymer, it is also envisaged to produce a material in a non-crosslinked form and to produce the crosslinked network subsequently in a mould under thermal conditions.

The invention will be further described with reference to the following Examples.

Example of 90/10 Mole Ratio VP/Phenethyl Methacrylate Gel 33.6 g. of vinyl pyrrolidone and 6.4 g. of phenethyl methacrylate were mixed together. To the mixture was added 0.27 g. of a crosslinking agent the specific member chosen being allyl methacrylate. Finally 0.12 g. of azobisisobutyrodinitrile (AZBN) was added as catalyst.

The mixture was put into a mould and degassed. The bulk of the polymerisation was carried out in a constant temperature enclosure between 45°-55° C. with the exclusion of oxygen for up to 24 hours. Polymerisation was completed by heating the mould at 100°-120° e.g. 110° C for 1-10 hours.

The resulting polymer had a water uptake of 73.5 (based upon the total eventual hydrogel) and an oxygen permeability, ml (STP cm./cm$^2$. sec cm(Hg) $\times$ 10$^{10}$) i.e. measured in milliliters at STP times centimeters thickness per square centimeter area, per second, per centimeter mercury pressure, $\times$ 10$^{10}$) of about 19.9. Moreover, the ultimate tensile strength in kilograms per square centimeter was 5.5, while the load to 10% elongation i.e. "10% T" (a measure of the stiffness of the material) was 0.9 kgf per square cm.

Water uptake was measured as uptake from physiological saline (0.9% NaCl in distilled water) at 20° C. The samples were refluxed in the saline for 16 hours and thereafter allowed to soak in fresh saline for 3 days. Percentage uptake is based on total, i.e. gel, weight.

Ultimate tensile strength (UTS) was measured by cutting out of swollen cast sheet, as described in ASTM D 1708, dumbbell-shaped samples which were then aged as above. The gauge length was 1 inch and the speed of the jaws of the Instron test machine was 2 inches per minute, the sample being immersed in saline for the duration of the test. The results are measured in Kgf/sq. cm.

The "10% T" denote the force required for 10% elongation, and is measured from the graph obtained during the UTS test above.

Ultimate tensile strength is a measure of the strength of the material, and "10% T" an indication of its stiffness, i.e. flexibility, (the higher the force the stiffer the material). The saline uptake, and the oxygen permeability are related characteristics.

Polymers as described above can be made into contact lenses as follows.

Bulk polymerisation is carried out under the time and temperature conditions described above in a vessel such as to give a rod of polymer of circular cross-section 12.7 mm in diameter and 30 cm long. This rod was sliced into "buttons" 6 mm thick. The buttons were latched to a calculated size, depending upon the optical prescription for the lens and upon the known swellability of the polymer. The latched shapes so produced were hydrated in sterile physiological saline at room temperature to give an overall diameter between 17.3 and 17.5 mm, thus providing a clear, very soft, and very flexible contact lens. It was found in use such a lens gave good visual acuity and visual stability over a period, with no significant water loss from its structure.

The invention will be further described with reference to the following table, which indicates certain properties of various methacrylic esters used as copolymerizable monomers with vinyl pyrrolidone in the molar proportions (and hence weight proportions) listed, the polymer samples having been made by the procedure as described above, using the crosslinking agents shown.

| CONSTITUENTS (METHACRYLIC ESTER | WT.% | MOLE % CROSS-LINKING AGENT | % SALINE UPTAKE OF RESULTING GEL (20°) | OXYGEN PERM. (20° C) | TENSILE kgf/cm$^2$ | LOAD 10% T. |
|---|---|---|---|---|---|---|
| VP/Benzyl | 88.2/21.8 | .64 Allyl MA | 67 | — | — | — |
| VP/Benzyl | 85/15 | .64 " | 73 | — | 6.6* | 1.5 |
| VP/Phenoxyethyl | 75.5/24.5 | .64 " | 69. | — | — | — |
| VP/Phenoxyethyl | 83/17 | .64 " | 73 | — | 8.3* | 1.3 |
| VP/Phenethyl | 70/30 | .64 " | 60 | — | stiff, creeps | — |
| VP/Phenethyl | 84/16 | .64 " | 73. | 19.9 | 5.5 | 0.9 |
| VP/Phenethyl | 85.5/14.5 | .64 " | 74 | — | — | — |
| VP/Phenethyl | 87/13 | .64 " | 73.5 | — | 4.1 | 0.8 |
| " | 88.5/11.5 | .64 " | 76.4 | — | 3.25 | .55 |
| " | 91.5/ 8.5 | .64 " | 78 | 25 | 1.6 | .45 |
| " | 87/13 | .4 " | 76.5 | — | 4.8 | .6 |
| " | " | .3 " | 79.5 | 28.5 | 4.4 | .55 |
| " | " | .2 GALEMA | 79 | — | 3.7 | .43 |
| " | " | .2 HALEMA | 80 | — | 3.75 | .41 |
| " | " | .2 DALEMA | 82 | 31 | 5.1 | .4 |
| " | " | .25 TRALEMA | 80.5 | 30.5 | 6.7 | .42 |
| VP/Benzyl | " | " | 79 | — | 9.0 | .72 |
| VP/Phenyl | " | " | 77 | — | 7.9 | 1.7 |
| VP/Phenoxyethyl | 87/13 | .25 TRALEMA | 79.7 | 29.5 | 6.9 | .47 |
| VP/p-Methoxyphenyl | " | " | 77.6 | — | 6.7 | .77 |
| VP/p-Methoxybenzyl | " | " | 81.8 | — | 8.0 | .37 |

-continued

| CONSTITUENTS (METHACRYLIC ESTER | WT.% | MOLE % CROSS-LINKING AGENT | % SALINE UPTAKE OF RESULTING GEL (20°) | OXYGEN PERM. (20° C) | TENSILE kgf/cm² | LOAD 10% T. |
|---|---|---|---|---|---|---|
| VP/p-Naphthyl | " | " | 74.3 | — | 13.9 | 4.4 |
| VP/4-Phenyl-phenyl | " | " | 72.8 | — | 15.3 | 3.8 |
| VP/4-Benzyl-phenyl | " | " | 75.0 | — | 14.0 | 2.3 |
| VP/4-t.Butyl phenyl | " | " | 69.5 | — | 15.2 | 10.6 |
| (COMPARISON) VP/Methyl MA | 75/25 | " | 76 | — | 3.0 | .33 |
| (COMPARISON) VP/Methyl MA | 80/20 | " | 80.5 | — | 1.7 | .22 |

GALEMA = 3-Allyloxy-2-hydroxy-propyl methacrylate
HALEMA = 2-Allyloxy ethyl MA
DALEMA = 2-(2-Allyloxy ethoxy)-ethyl MA
TRALEMA = 2-(2-Allyloxy-ethoxy ethoxy) - ethyl MA.

We claim:

1. A lightly crosslinked hydrogen copolymeric material with an uptake of physiological saline of between 65% and 85%, by weight, based on the total weight of gel, said material being formed from (1) at least one water soluble N-vinyl lactam and (2) as a comonomer, not more than 15 mole percent of at least one compound of formula:

$$CH_2=C-CO-X-R^2$$
$$|$$
$$R^1$$

wherein X is selected from the group consisting of —NH— and —O—; $R^1$ is selected from the group consisting of hydrogen and alkyl groups containing from 1 to 4 carbon atoms; and $R^2$ is selected from the group consisting of (A) substituted and unsubstituted phenyl and naphthyl wherein the substituent groups are selected from the group consisting of benzyl, alkyl containing from 1 to 4 carbon atoms, alkoxy containing from 1 to 4 carbon atoms, halo, phenyl, and alkyl phenyl wherein the alkyl group contains from 1 to 4 carbon atoms; and (B) an alkyl group containing from 1 to 6 carbon atoms wherein the alkyl group is substituted by at least one member selected from the group consisting of substituted phenyl, phenyloxy, naphthyl and naphthyloxy, wherein the substituents are selected from the group consisting of benzyl, alkyl containing from 1 to 4 carbon atoms, alkoxy containing from 1 to 4 carbon atoms, halo, phenyl, and alkylphenyl wherein the alkyl group contains from 1 to 4 carbon atoms, and wherein when said member substituted on the alkyl group is substituted or unsubstituted phenyloxy or naphthyloxy, said member is substituted on a carbon atom of the alkyl group other than the carbon atom adjacent to the —X— group.

2. A lightly crosslinked copolymer as claimed in claim 1 wherein the X is —O—.

3. A lightly crosslinked copolymer as claimed in claim 2 wherein $R^2$ is (A).

4. A lightly crosslinked copolymer as claimed in claim 3 wherein $R^1$ is methyl.

5. A lightly crosslinked copolymer as claimed in claim 4 wherein the N-vinyl lactam is N-vinyl-2-pyrrolidone.

6. A lightly crosslinked copolymer as claimed in claim 5 wherein $R^2$ is selected from the group consisting of phenyl, 2-naphthyl, (3-phenyl) phenyl, (4-phenyl) phenyl, (3-benzyl) phenyl, (4-benzyl) phenyl, (4-t-butyl) phenyl and p-methoxyphenyl.

7. A lightly crosslinked copolymer as claimed in claim 6 wherein the copolymer is crosslinked with up to 5%, by weight, of a crosslinking agent.

8. A lightly crosslinked copolymer as claimed in claim 6 wherein the copolymer is crosslinked with up to 2%, by weight, of a crosslinking agent having two functional groups which differ in reactivity.

9. A lightly crosslinked copolymer as claimed in claim 8 wherein the crosslinking agent is selected from the group consisting of compounds having the following structural formulae:

$$CH_2=C-CO-(OCH_2CH_2)_n-O-R^3 \quad (1)$$
$$|$$
$$CH_3$$

and $$CH_2=C-CO-OCH_2-CHOH-CH_2-O-R_3 \quad (2)$$
$$|$$
$$CH_3$$

wherein $R^3$ is selected from the group consisting of allyl and vinyl and $n$ is 0 to 4.

10. A lightly crosslinked copolymer as claimed in claim 2 wherein $R^2$ is (B).

11. A lightly crosslinked copolymer as claimed in claim 10 wherein $R^1$ is methyl.

12. A lightly crosslinked copolymer as claimed in claim 11 wherein the N-vinyl lactam is N-vinyl-2-pyrrolidone.

13. A lightly crosslinked copolymer as claimed in claim 12 wherein $R^2$ is selected from the group consisting of phenyl, 2-naphthyl, (3-phenyl) phenyl, (4-phenyl) phenyl, (3-phenyl) phenyl, (4-benzyl) phenyl, phenoxy, 2-naphthyloxy, (3-phenyl) phenoxy, (4-phenyl) phenoxy, (3benzyl) phenoxy, (4-benzyl) phenoxy, (4-t-butyl) phenyl and p-methoxyphenyl.

14. A lightly crosslinked copolymer as claimed in claim 13 wherein the copolymer is crosslinked with up to 5%, by weight, of a crosslinking agent.

15. A lightly crosslinked copolymer as claimed in claim 13 wherein the copolymer is crosslinked with up to 2%, by weight, of a crosslinking agent having two functional groups which differ in reactivity.

16. A lightly crosslinked copolymer as claimed in claim 15 wherein the crosslinking agent is selected from the group consisting of compounds having the following structural formulae:

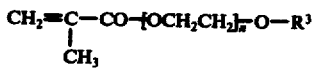

and

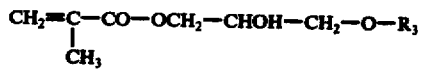

wherein R³ is selected from the group consisting of allyl and vinyl and n is 0 to 4.

17. A lightly crosslinked hydrogel copolymeric material with an uptake of physiological saline of between 65% and 85%, by weight, based on the total weight of gel, said material being formed from (1) N-vinyl-2-pyrrolidone and (2) as a comonomer at least one member selected from the group consisting of benzylmethacrylate, phenoxyethylmethacrylate, phenethylmethacrylate, phenylmethacrylate, phenoxyethylmethacrylate, p-methoxyphenylmethacrylate, p-methoxybenzylmethacrylate, β-naphthylmethacrylate, 4-phenyl-phenylmethacrylate, 4-benzyl-phenylmethacrylate and 4-t-butylphenylmethacrylate.

18. A lightly crosslinked copolymer as claimed in claim 17 wherein the copolymer is crosslinked with up to 2%, by weight, of a crosslinking agent selected from the group consisting of 3-allyloxy-2-hydroxy-propylmethacrylate, 2-allyloxyethylmethacrylate, 2-(2-allyloxyethoxy)-methylmethacrylate and 2-(2-allyloxy-ethoxy ethoxy-ethylmethacrylate, 19. A lightly crosslinked copolymer as claimed in claim 18 wherein the comonomer (2) is phenethylmethacrylate.

20. A lightly crosslinked copolymer as claimed in claim 17 wherein the comonomer is phenethylmethacrylate.

21. A contact lens comprised of a polymer as defined in claim 2.

22. A contact lens comprised of a polymer as defined in claim 6.

23. A contact lens comprised of a polymer as defined in claim 9.

24. A contact lens comprised of a polymer as defined in claim 10.

25. A contact lens comprised of a polymer as defined in claim 13.

26. A contact lens comprised of a polymer as defined in claim 16.

27. A contact lens comprised of a polymer as defined in claim 17.

28. A contact lens comprised of a polymer as defined in claim 19.

29. A method of producing a lightly crosslinked copolymer as claimed in claim 1 in which the hydrophilic component (1) and the hydrophobic component (2), together with not more than 5% of crosslinking agent and a catalyst to promote free-radical polymerization are heated to 45° to 55° C for up to 24 hours in the absence of oxygen and subsequently heated at 100° to 120° C for between 1 and 10 hours.

* * * * *